United States Patent
Trail (10) Patent No.: US 10,154,254 B2
(45) Date of Patent: Dec. 11, 2018

(54) TIME-OF-FLIGHT DEPTH SENSING FOR EYE TRACKING

(71) Applicant: Facebook Technologies, LLC, Menlo Park, CA (US)

(72) Inventor: Nicholas Daniel Trail, Bothell, WA (US)

(73) Assignee: Facebook Technologies, LLC, Menlo Park, CA (US)

(*) Notice: Subject to any disclaimer, the term of this patent is extended or adjusted under 35 U.S.C. 154(b) by 166 days.

(21) Appl. No.: 15/408,104

(22) Filed: Jan. 17, 2017

(65) Prior Publication Data
US 2018/0205943 A1    Jul. 19, 2018

(51) Int. Cl.
*H04N 13/383*    (2018.01)
*G06T 7/73*    (2017.01)
(Continued)

(52) U.S. Cl.
CPC ........... *H04N 13/383* (2018.05); *G06F 3/013* (2013.01); *G06K 9/0061* (2013.01);
(Continued)

(58) Field of Classification Search
CPC .................................................. H04N 13/383
See application file for complete search history.

(56) References Cited

U.S. PATENT DOCUMENTS 8,847,850 B1 *  9/2014  Cho ...................... G02B 27/017
                                                        345/7
9,202,443 B2 *  12/2015  Perez ...................... G02B 27/02
(Continued)

FOREIGN PATENT DOCUMENTS

JP          3298081 B2    7/2002
JP       2014-219621 A    11/2014
(Continued)

OTHER PUBLICATIONS

PCT International Search Report and Written Opinion, PCT Application No. PCT/US2017/012346, dated Mar. 30, 2017, 13 pages.
(Continued)

*Primary Examiner* — James M Pontius
(74) *Attorney, Agent, or Firm* — Fenwick & West LLP (57) ABSTRACT

A head-mounted display (HMD) includes an eye tracking system that determines user's eye tracking information based on depth information derived from time-of-flight methods. The eye tracking system includes an illumination source, an imaging device and a controller. The illumination source illuminates the user's eye with a temporally varying irradiance pattern. The imaging device includes a detector that captures temporal phase shifts (temporal distortions) caused by a local geometry and the illumination pattern being reflected from a portion of the eye. The detector comprises multiple pixels, each pixel having multiple units for capturing, over multiple time instants, light signals related to the temporally distorted illumination pattern. The controller determines phase differences between the temporally distorted illumination pattern and the temporally varying irradiance pattern, based on the captured light signals. The controller determines depth information related to eye surfaces and updates a model of the eye, based on the phase differences.

20 Claims, 5 Drawing Sheets

(51) Int. Cl.
*G06T 7/50* (2017.01)
*G06K 9/00* (2006.01)
*G06F 3/01* (2006.01)
*H04N 13/211* (2018.01)
*H04N 13/344* (2018.01)

(52) U.S. Cl.
CPC ............ *G06K 9/00604* (2013.01); *G06T 7/50* (2017.01); *G06T 7/73* (2017.01); *H04N 13/211* (2018.05); *H04N 13/344* (2018.05); *G06T 2207/10012* (2013.01); *G06T 2207/30201* (2013.01)

(56) References Cited

U.S. PATENT DOCUMENTS

| | | |
|---|---|---|
| 2006/0210111 A1 | 9/2006 | Cleveland et al. |
| 2007/0183293 A1 | 8/2007 | Murata et al. |
| 2013/0050070 A1 | 2/2013 | Lewis et al. |
| 2013/0176533 A1 | 7/2013 | Raffle et al. |
| 2014/0153102 A1 | 6/2014 | Chang |
| 2014/0211193 A1 | 7/2014 | Bloom et al. |
| 2015/0062558 A1 | 3/2015 | Koppal et al. |
| 2015/0102981 A1 | 4/2015 | Lee et al. |
| 2015/0181096 A1 | 6/2015 | Kasai et al. |
| 2015/0212326 A1 | 7/2015 | Kress et al. |
| 2016/0005179 A1 | 1/2016 | Petyushko et al. |
| 2017/0123526 A1* | 5/2017 | Trail ................. G06F 3/041 |
| 2017/0192499 A1* | 7/2017 | Trail ................. G06F 3/013 |
| 2017/0206660 A1 | 7/2017 | Trail |
| 2017/0293146 A1* | 10/2017 | Nicholls ............ G02B 27/0172 |
| 2018/0101989 A1* | 4/2018 | Frueh ................. G06F 17/3025 |
| 2018/0196509 A1* | 7/2018 | Trail ................. G06F 3/013 |

FOREIGN PATENT DOCUMENTS

| | | |
|---|---|---|
| KR | 10-2013-0011692 A | 1/2013 |
| KR | 10-2014-0144510 A | 12/2014 |

OTHER PUBLICATIONS

PCT International Search Report and Written Opinion, PCT Application No. PCT/US2016/059938, dated Dec. 20, 2016, 12 pages.
PCT International Search Report and Written Opinion, PCT Application No. PCT/US2016/017397, dated Aug. 16, 2016, 21 pages.
U.S. Appl. No. 15/407,701, filed Jan. 17, 2017, Inventors Nicholas Daniel Trail et al.
U.S. Appl. No. 14/963,126, filed Dec. 8, 2015, Inventors Douglas Robert Lanman et al.
U.S. Appl. No. 15/366,412, filed Dec. 1, 2016, Inventor Nicholas Daniel Trail.
Machine translation of JP 2014-219621, published Nov. 20, 2014, 15 pages.

* cited by examiner

TIME-OF-FLIGHT DEPTH SENSING FOR EYE TRACKING

BACKGROUND

The present disclosure generally relates to eye tracking, and specifically relates to using time-of-flight based depth information for eye tracking in virtual reality and/or augmented reality applications.

Eye tracking refers to the process of detecting the direction of a user's gaze, which may comprise detecting the angular orientation of the eye in three-dimensional space. Eye tracking may further comprise detecting the location of the eye (e.g., the center of the eye), the torsion (i.e., the roll of the eye about the pupillary axis) of the eye, the shape of the eye, the current focal distance of the eye, the dilation of the pupil, other features of the eye's state, or some combination thereof. One known technique for eye tracking is capturing video images of a user and identifying the orientation of the user's pupils using a machine vision algorithm. However, this technique requires substantial computing resources, and is susceptible to occlusion of the eye by eyelashes and eyelids. Furthermore, this method is dependent on the contrast between the iris and the pupil, which is not invariant across users. Thus, video based pupil tracking may not be able to accurately track the eyes of certain users. Similarly, this technique may place constraints on the proximity of the camera to the user's eye. Furthermore, this technique may perform poorly when the camera is located off the axis of the user's gaze. However, when eye tracking is used in an HMD, it may be preferred that the detection element of the eye tracking system be small, be close to the eye, and be off the axis of the user's gaze.

SUMMARY

Embodiments of the present disclosure support a head-mounted display (HMD) that comprises an electronic display, an optical assembly, and an eye tracking system. The HMD may be, e.g., a virtual reality (VR) system, an augmented reality (AR) system, a mixed reality (MR) system, or some combination thereof. The electronic display is configured to display content to a user wearing the HMD, and the optical assembly is configured to direct light from the electronic display to an exit pupil of an eye of the user. The eye tracking system includes an illumination source, an imaging device (camera) and a controller coupled to the imaging device or being part of the imaging device. The illumination source illuminates the eye with a temporally varying irradiance pattern producing a controlled illumination pattern on a portion of the eye. The imaging device captures perceived temporal distortions in the illumination pattern (i.e., a temporally distorted illumination pattern) associated with the portion of the eye and a local geometry of the eye. A temporal distortion is defined by a change in a measured phase of an output temporal frequency or signal, both in absolute and relative terms across an imaged area or region. The imaging device includes a detector comprising a plurality of pixels, wherein each pixel is associated with multiple storage units for capturing light signals related to the temporally distorted illumination pattern captured in multiple time instants. The controller determines one or more phase differences between the temporally distorted illumination pattern and the temporally varying irradiance pattern, based on the light signals captured in the storage units during the multiple time instants. Based on the one or more phase differences, the controller calculates one or more distances from the detector to one or more surfaces of the eye. Based on the one or more distances, the controller updates a model of the eye and estimates a position and orientation of the eye based on the updated model.

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

DETAILED DESCRIPTION

Disclosed embodiments include an eye tracking system integrated into a head-mounted display (HMD). The HMD may be part of, e.g., a virtual reality (VR) system, an augmented reality (AR) system, a mixed reality (MR) system, or some combination thereof. The HMD may further include an electronic display and an optical assembly. The eye tracking system presented herein includes an illumination source and an imaging device. The illumination source projects a temporal irradiance pattern onto a portion of an eye of a user wearing the HMD. The imaging device detects light reflected from at least one surface of the user's eye. The eye tracking system updates a model of the user's eye using depth information derived from time-of-flight methods applied on the reflected light captured by the imaging device. The eye tracking system determines a position and orientation of the user's eye (eye-gaze) based on the updated model of the user's eye.

Figure 1:
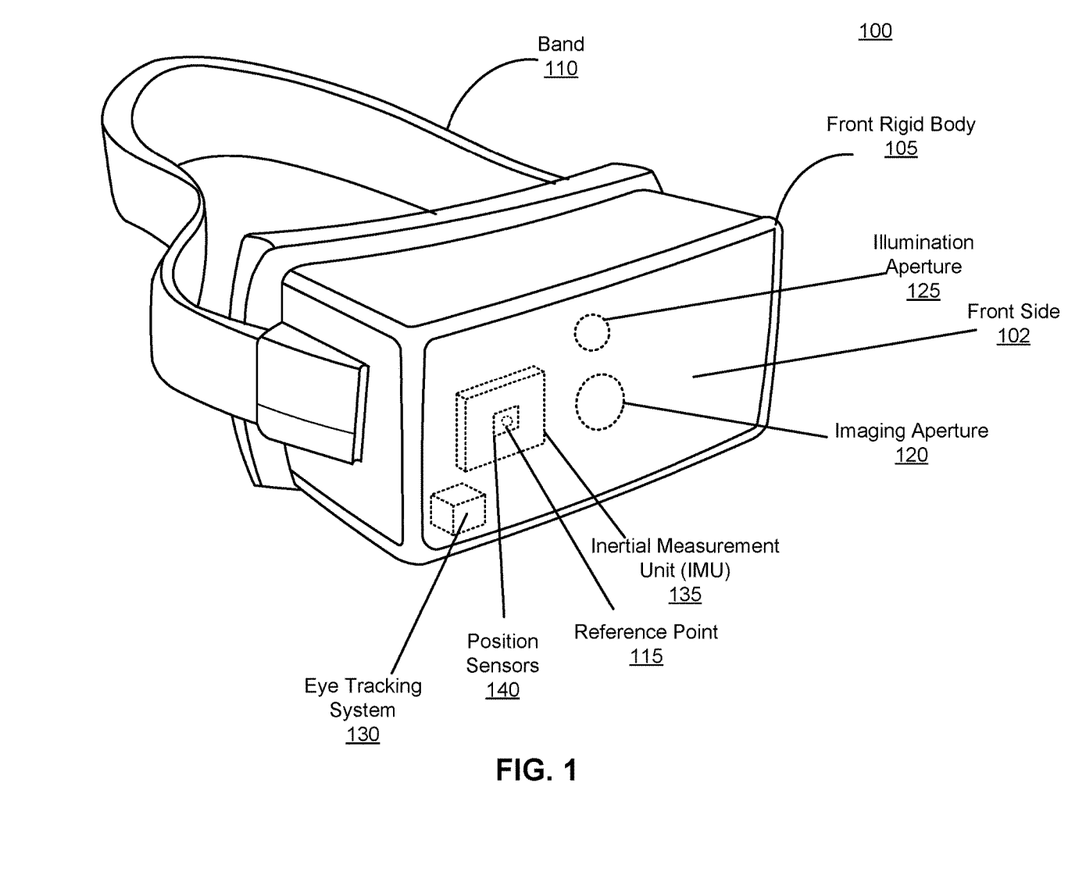
FIG. 1 is a diagram of a head-mounted display (HMD), in accordance with an embodiment.

FIG. 1 is a diagram of a HMD 100, in accordance with an embodiment. The HMD 100 may be part of, e.g., a VR system, an AR system, a MR system, or some combination thereof. In embodiments that describe an AR system and/or a MR system, portions of a front side 102 of the HMD 100 are at least partially transparent in the visible band (~380 nm to 750 nm), and portions of the HMD 100 that are between the front side 102 of the HMD 100 and an eye of the user are at least partially transparent (e.g., a partially transparent electronic display). The HMD 100 includes a front rigid body 105, a band 110, and a reference point 115. In some embodiments, the HMD 100 shown in FIG. 1 also includes a depth camera assembly (DCA) configured to determine depth information of a local area surrounding some or all of the HMD 100. In these embodiments, the HMD 100 would also include an imaging aperture 120 and an illumination aperture 125, and an illumination source of the DCA would emit light (e.g., structured light) through the illumination aperture 125. And an imaging device of the DCA would capture light from the illumination source that is reflected/ scattered from the local area through the imaging aperture 120.

In one embodiment, the front rigid body 105 includes one or more electronic display elements (not shown in FIG. 1), one or more integrated eye tracking systems 130 (e.g., one eye tracking system 130 for each eye of a user wearing the HMD 100), an Inertial Measurement Unit (IMU) 135, one or more position sensors 140, and the reference point 115. In the embodiment shown by FIG. 1, the position sensors 140 are located within the IMU 135, and neither the IMU 135 nor the position sensors 140 are visible to a user of the HMD 100. The IMU 135 is an electronic device that generates fast calibration data based on measurement signals received from one or more of the position sensors 140. A position sensor 140 generates one or more measurement signals in response to motion of the HMD 100. Examples of position sensors 140 include: one or more accelerometers, one or more gyroscopes, one or more magnetometers, another suitable type of sensor that detects motion, a type of sensor used for error correction of the IMU 135, or some combination thereof. The position sensors 140 may be located external to the IMU 135, internal to the IMU 135, or some combination thereof.

The eye tracking system 130 estimates a position and angular orientation of an eye of a user wearing the HMD 100. The position and angular orientation of the eye corresponds to the direction of the user's gaze within the HMD 100. The orientation of the user's eye is defined herein as the direction of the foveal axis, which is the axis between the fovea (an area on the retina of the eye with the highest concentration of photoreceptors) and the center of the eye's pupil. In general, when user's eyes are fixed on a point, the foveal axes of the user's eyes intersect that point. The pupillary axis is another axis of the eye which is defined as the axis passing through the center of the pupil which is perpendicular to the corneal surface. The pupillary axis does not, in general, directly align with the foveal axis. Both axes intersect at the center of the pupil, but the orientation of the foveal axis is offset from the pupillary axis by approximately −1° to 8° laterally and ±4° vertically. Because the foveal axis is defined according to the fovea, which is located in the back of the eye, the foveal axis can be difficult or impossible to detect directly in some eye tracking embodiments. Accordingly, in some embodiments, the orientation of the pupillary axis is detected and the foveal axis is estimated based on the detected pupillary axis.

In general, movement of an eye corresponds not only to an angular rotation of the eye, but also to a translation of the eye, a change in the torsion of the eye, and/or a change in shape of the eye. The eye tracking system 130 may also detect translation of the eye: i.e., a change in the position of the eye relative to the eye socket. In some embodiments, the translation of the eye is not detected directly, but is approximated based on a mapping from a detected angular orientation. Translation of the eye corresponding to a change in the eye's position relative to the detection components of the eye tracking system 130 may also be detected. Translation of this type may occur, for example, due to shift in the position of the HMD 100 on a user's head. The eye tracking system 130 may also detect the torsion of the eye, i.e., rotation of the eye about the pupillary axis. The eye tracking system 130 may use the detected torsion of the eye to estimate the orientation of the foveal axis from the pupillary axis. The eye tracking system 130 may also track a change in the shape of the eye, which may be approximated as a skew or scaling linear transform or a twisting distortion (e.g., due to torsional deformation). The eye tracking system 130 may estimate the foveal axis based on some combination of the angular orientation of the pupillary axis, the translation of the eye, the torsion of the eye, and the current shape of the eye.

The eye tracking system 130 provides for means to relate an exterior three-dimensional surface of cornea and sclera in the eye to its gaze position, in addition to an optical power through the front corneal surface and interaction with the pupil surface. The sclera is the relatively opaque (usually visibly white) outer portion of the eye, which is often referred to as the "white of the eye." The cornea is the curved surface covering the iris and the pupil of the eye. The eye tracking system 130 allows for a path to measure eye surfaces/features off-axis (from the direct pupil gaze) through time-of-flight depth sensing methods. This is achievable herein by an implementation of the eye tracking system 130 that includes an illumination source and an imaging device (camera) set at a defined angle to an eye-box, i.e., an imaged region of interest. An eye-box represents a three-dimensional volume at an output of a HMD in which the user's eye is located to receive image light. The illumination source in the eye tracking system 130 projects a temporally varying irradiance pattern on all or a portion of the eye and surrounding facial regions. In some embodiments, the projected temporally varying irradiance pattern can be sinusoidal or square wave in nature, i.e., an intensity of emitted light varies over time based on variation of the sinusoidal or square wave carrier signal. When the projected temporally varying irradiance light pattern is mapped through time onto the cornea, sclera, pupil of the eye, etc., a distortion (i.e., warp) in the temporally varying irradiance pattern occurs that encodes three-dimensional coordinates of various surfaces of the eye relative to the camera's principal axis and position. The imaging device (camera) of the eye tracking system 130 is generally (although not required to be) oriented on a different axis than the illumination source and captures illumination pattern on the eye, i.e., performs "scanning" of the eye. The imaging device detects intensities of light that correspond to the temporal distortion of the light pattern projected onto surfaces of the eye and a surrounding skin. Based on detecting the deformation of the illumination pattern, the eye tracking system 130 updates a model of the eye using depth information derived from time-of-flight phase retrieval methods. By leveraging the asymmetry in the cornea, sclera, and pupil surface, a fit to the surface geometry can be made as a baseline and projected during use to provide a real-time estimate of the user's gaze and orientation of the eye. The eye tracking system 130 can also estimate the pupillary axis, the translation of the eye, the torsion of the eye, and the current shape of the eye based on the depth information derived from time-of-flight phase retrieval methods.

As the orientation and position may be determined for both eyes of the user, the eye tracking system 130 is able to determine where the user is looking. The HMD 100 can use the orientation and position of the eye to, e.g., determine an inter-pupillary distance (IPD) of the user, determine gaze direction, introduce depth cues (e.g., blur image outside of the user's main line of sight), collect heuristics on the user interaction in the VR/AR/MR media (e.g., time spent on any particular subject, object, or frame as a function of exposed stimuli), some other function that is based in part on the orientation of at least one of the user's eyes, or some combination thereof. Determining a direction of a user's gaze may include determining a point of convergence based on the determined orientations of the user's left and right eyes. A point of convergence may be the point that the two foveal axes of the user's eyes intersect (or the nearest point between the two axes). The direction of the user's gaze may be the direction of a line through the point of convergence and though the point halfway between the pupils of the user's eyes.

Figure 2:
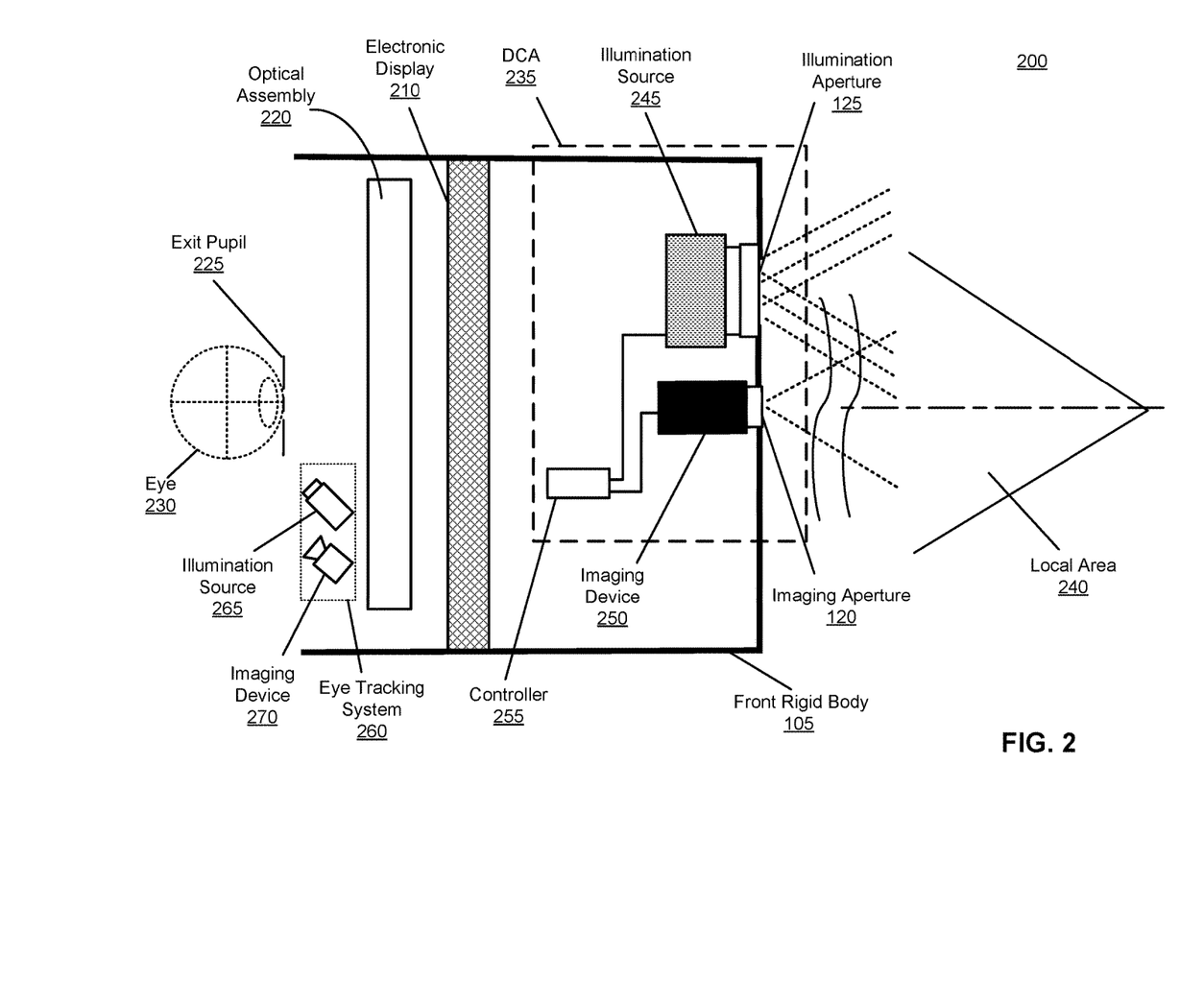
FIG. 2 is a cross section of a front rigid body of the HMD in FIG. 1 that includes an eye tracking system, in accordance with an embodiment.

FIG. 2 is a cross section 200 of the front rigid body 105 of the embodiment of the HMD 100 shown in FIG. 1. As shown in FIG. 2, the front rigid body 105 includes an electronic display 210 and an optical assembly 220 that together provide image light to an exit pupil 225. The exit pupil 225 is the location of the front rigid body 105 where a user's eye 230 is positioned. For purposes of illustration, FIG. 2 shows a cross section 200 associated with a single eye 230, but another optical assembly 220, separate from the optical assembly 220, provides altered image light to another eye of the user.

The electronic display 210 generates image light. In some embodiments, the electronic display 210 includes an optical element that adjusts the focus of the generated image light. The electronic display 210 displays images to the user in accordance with data received from a console (not shown in FIG. 2). In various embodiments, the electronic display 210 may comprise a single electronic display or multiple electronic displays (e.g., a display for each eye of a user). Examples of the electronic display 210 include: a liquid crystal display (LCD), an organic light emitting diode (OLED) display, an inorganic light emitting diode (ILED) display, an active-matrix organic light-emitting diode (AMOLED) display, a transparent organic light emitting diode (TOLED) display, some other display, a projector, or some combination thereof. The electronic display 210 may also include an aperture, a Fresnel lens, a convex lens, a concave lens, a diffractive element, a waveguide, a filter, a polarizer, a diffuser, a fiber taper, a reflective surface, a polarizing reflective surface, or any other suitable optical element that affects the image light emitted from the electronic display. In some embodiments, one or more of the display block optical elements may have one or more coatings, such as anti-reflective coatings.

The optical assembly 220 magnifies received light from the electronic display 210, corrects optical aberrations associated with the image light, and the corrected image light is presented to a user of the HMD 100. At least one optical element of the optical assembly 220 may be an aperture, a Fresnel lens, a refractive lens, a reflective surface, a diffractive element, a waveguide, a filter, a reflective surface, a polarizing reflective surface, or any other suitable optical element that affects the image light emitted from the electronic display 210. Moreover, the optical assembly 220 may include combinations of different optical elements. In some embodiments, one or more of the optical elements in the optical assembly 220 may have one or more coatings, such as anti-reflective coatings, dichroic coatings, etc. Magnification of the image light by the optical assembly 220 allows elements of the electronic display 210 to be physically smaller, weigh less, and consume less power than larger displays. Additionally, magnification may increase a field of view of the displayed media. For example, the field of view of the displayed media is such that the displayed media is presented using almost all (e.g., 110 degrees diagonal), and in some cases all, of the user's field of view. In some embodiments, the optical assembly 220 is designed so its effective focal length is larger than the spacing to the electronic display 210, which magnifies the image light projected by the electronic display 210. Additionally, in some embodiments, the amount of magnification may be adjusted by adding or removing optical elements.

The front rigid body 105 further includes a DCA 235 for determining depth information of one or more objects in a local area 240 surrounding some or all of the HMD 100. The DCA 235 includes an illumination source 245, an imaging device (camera) 250, and a controller 255 that may be coupled to both the illumination source 245 and the imaging device 250. The illumination source 245 emits light (e.g., structured light) through the illumination aperture 125. The illumination source 245 may be composed of a plurality of laser-type light emitters on a single substrate configured to simultaneously or in different time instants (e.g., controlled by the controller 260) emit a plurality of light beams, e.g., in the form of a structured light pattern. The imaging device 250 captures light from the illumination source 245 that is reflected/scattered from the local area 240 through the imaging aperture 120. The controller 260 may be configured to determine depth information of the one or more objects in the local area 240 based on the captured reflected/scattered light.

As shown in FIG. 2, the front rigid body 105 further includes an eye tracking system 260 placed between the user's eye 230 and the optical assembly 220 configured to determine and track a position and orientation of the user's eye 230. The eye tracking system 260 is an embodiment of the eye tracking system 130 in FIG. 1. In alternate embodiments, the eye tracking system 260 is placed between the optical assembly 220 and the electronic display 210 or within the optical assembly 220. The eye tracking system 260 includes an illumination source 265 and an imaging device (camera) 270. The illumination source 265 emits light onto a portion of the eye 230. The imaging device 270 captures light reflected from the portion of the eye 230 illuminated by the illumination source 265. A controller (not shown in FIG. 2) coupled to the imaging device 270 or integrated into the imaging device 270 may be configured to determine eye tracking information for the user's eye 230. The determined eye tracking information may comprise information about a position and orientation of the user's eye 230 in an eye-box, i.e., information about an angle of an eye-gaze. The components of the eye tracking system 260 are positioned outside an optical axis of the front rigid body 105, i.e., the illumination source 265 and the imaging device 270 are positioned outside of a primary optical path of the electronic display 210, whether a transmitted or reflected primary optical path of the electronic display 210. Instead, the illumination source 265 and the imaging device 270 are coupled through one or more non-primary direct or reflected optical paths to the user's eye 230. The one or more non-primary optical paths may encompass at least part of the primary optical path of the electronic display 210. Based on the determined and tracked position and orientation of the user's eye 230 (i.e., eye-gaze), the HMD 100 may adjust presentation of an image displayed on the electronic display 210. In some embodiments, the HMD 100 may adjust resolution of the displayed image based on the eye tracking information. A maximum pixel density for displaying an image on the electronic display 210 can be provided only in a foveal region of the determined eye-gaze, whereas a lower resolution display is employed in other regions, without negatively affecting the user's visual experience. More details about implementation and operation of the eye tracking system 260 are further described below in conjunction with FIGS. 3 and 4.

Figure 3:
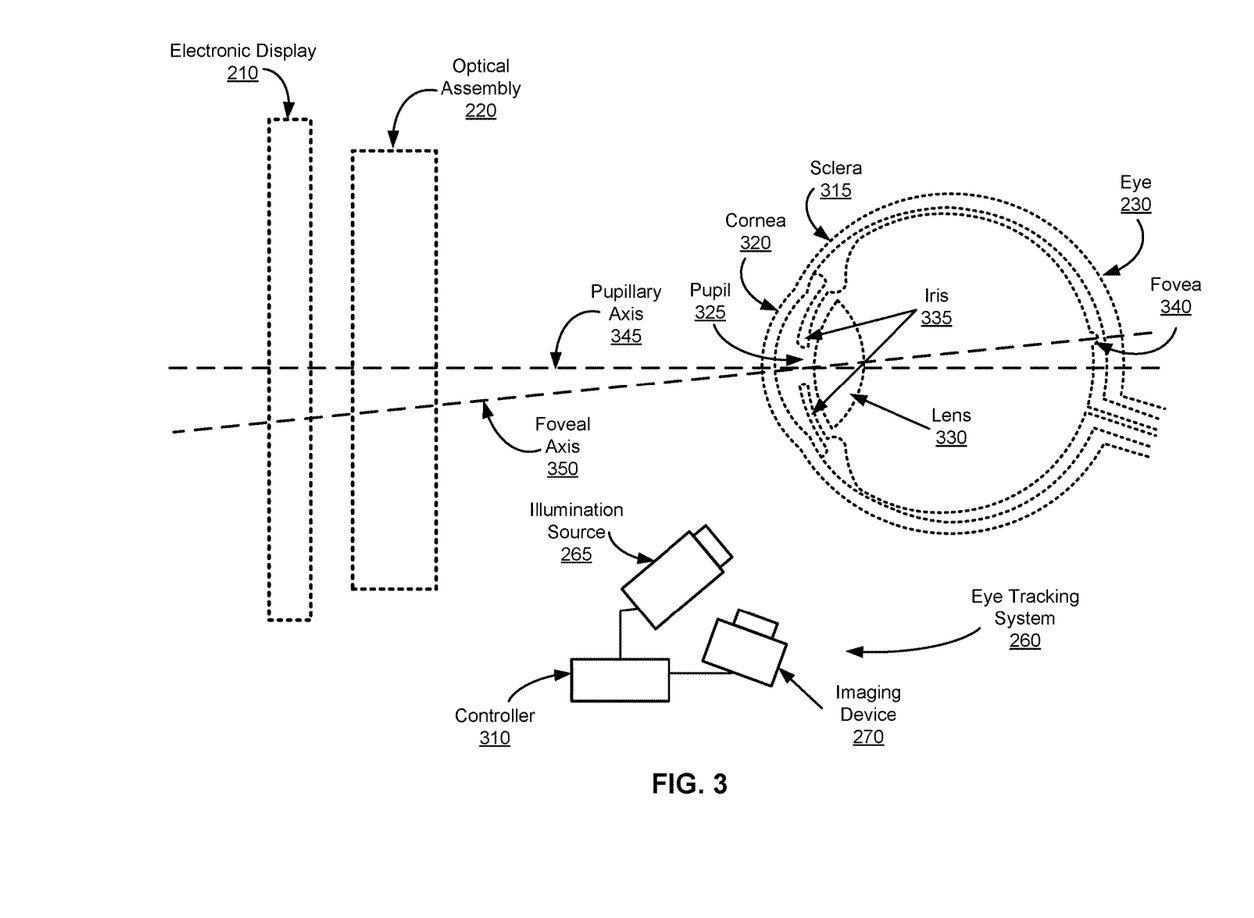
FIG. 3 illustrates an example eye tracking system that determines eye tracking information, which may be part of the HMD in FIG. 1, in accordance with an embodiment.

FIG. 3 depicts details of the eye tracking system 260 in FIG. 2 which tracks the position and orientation of the user's eye 230 by repeatedly (e.g., temporally) scanning the eye 230 using time-of-flight phase retrieval for the distorted light reflected from surfaces of the user's eye 230 and surrounding surfaces. FIG. 3 includes a cross-section of the eye 230. The eye tracking system 260 includes the illumination source 265 and the imaging device (camera) 270, as being also shown in FIG. 2. The eye tracking system 260 further includes a controller 310 coupled to both the illumination source 265 and the imaging device 270, the controller 310 configured to determine a position and orientation of a single eye 230. The controller 310 is further configured to ensure synchronization between the illumination source 265 and the imaging device 270 by correlating to the imaging device 270 phase information associated with a temporally varying irradiance pattern emitted from the illumination source 265. In an alternate embodiment, the controller 310 is part of the imaging device 270. In alternate embodiments, multiple illumination sources or multiple imaging devices may be employed for a single eye. Similarly, for each of the user's eyes, a corresponding illumination source and imaging device may be employed.

The illumination source 265 emits a temporally varying irradiance pattern onto a portion of the eye 230. The illumination source 265 emits the light pattern in specific time periods controlled by the controller 310. In some embodiments, the emitted temporally varying irradiance pattern is a sinusoidal or square wave in nature comprising one or more frequencies, e.g., one or more frequencies between approximately 30 MHz and 10 GHz. When the emitted temporally varying irradiance pattern is a square wave, the temporally varying irradiance pattern comprises a single repeating time-basis. In some embodiments, the illumination source 265 may comprise an infrared light source (e.g., laser diode, light emitting diode, etc.) that emits infrared light (e.g., having one or more wavelengths above 750 nm) toward the eye 230. The illumination source 265 may emit a spread spectrum of infrared light, either naturally such as exhibited in light emitting diodes (LEDs) or through the generation of multiple emission points either physically present or optically such as through a diffuser, to reduce the coherence of the infrared light source. In some embodiments, due to constraints of geometry of the eye tracking system 260, the illumination source 265 outputs the temporally varying irradiance pattern having a single temporal frequency, which reduces data overhead, latency and data smear. In alternate embodiments, the illumination source 265 outputs the temporally varying irradiance pattern having N frequencies or N narrow bands with distinct center-frequencies. The temporally varying irradiance pattern having multiple frequencies facilitates mitigation of a multi-bounce effect that occurs when the light pattern reflected from at least one surface of the eye 230 further reflects from one or more other surfaces before reaching the imaging device 270. Additionally, in some embodiments, the illumination source 265 may be modulated in time, frequency, or both. Although the illumination source 265 is described herein as emitting light in the infrared spectrum, alternate embodiments include an illumination source 265 which emits light in non-infrared wavelengths, such as the visible spectrum (~390 nm to 700 nm).

In the context of a single eye of a user, the temporally varying irradiance pattern emitted from the illumination source 265 is incident upon a surface of a portion of the eye 230. The light pattern as received by the imaging device 270 is temporally distorted (phase offset across a scene) based in part on, e.g., the geometry of the illuminated surface and globally from the emitter to imaging device geometry, to form a distorted illumination pattern. A temporal distortion is defined by a change in a measured phase of an output temporal frequency or signal, both in absolute and relative terms across an imaged area or region, which may also include, e.g., an eye socket and/or eyelids. The variation in the measured phase of the temporal illumination pattern is indicative of the three-dimensional structure of a portion of the surface of the eye 230. In some embodiments, the portion of the eye covers the sclera 315, the cornea 320, or both. In some embodiments, the eye tracking system 260 covers the eye 230 and a significant region of skin/anatomy around a socket of the eye 230 (not shown in FIG. 3).

The imaging device 270 detects the temporally distorted light pattern on the portion of the eye 230 illuminated by the illumination source 265. The imaging device 270 may be an infrared camera (i.e., a camera designed to capture images in the infrared frequency). The imaging device 270 may be a near-infrared camera with digital image sensors sensitive to the bandwidth of light emitted by the illumination source 265. The imaging device 270 may include, although not limited to, a charge-coupled device (CCD) or complementary metal-oxide semiconductor (CMOS) digital image sensor and an optical element. The optical element may be one or more lenses, a high-pass, low-pass, or band-pass filter, a polarizer, an aperture stop, a diaphragm, some other optical element suitable for processing infrared light, or some combination thereof. The optical element outputs light which is captured and converted into a digital signal by the CCD or CMOS digital sensor. In some embodiments, the imaging device 270 comprises a detector that includes an array of pixels, such as an array of 240×320 pixels.

The imaging device 270 detects the temporally distorted illumination pattern and converts the captured light into a digital image. The imaging device 270 includes a detector (not shown in FIG. 3) that comprises a plurality of pixels, each pixel being associated with multiple storage units for capturing light intensities related to the temporally distorted illumination pattern captured during multiple time instants after being reflected from various surfaces of the eye 230. Each storage unit of a pixel in the detector of the imaging device 270 captures an intensity of a reflected light signal that has a specific phase shift relative to other reflected light signal whose intensity is captured in another storage unit of the same pixel, which may be controlled based on control signals generated by the controller 310. In one embodiment, four storage units are associated with each pixel in the detector, wherein light captured by a storage unit of a pixel has a 90 degree phase shift relative to light captured by another storage unit of the same pixel. In another embodiment, two storage units are associated with each pixel in the detector, wherein light captured by a storage unit of a pixel has a 180 degree phase shift relative to light captured by another storage unit of the same pixel. In yet another embodiment, three storage units are associated with each pixel in the detector, wherein light captured by a storage unit of a pixel has a 120 degree phase shift relative to light captured by another storage unit of the same pixel. In general, m storage units are associated with each pixel in the detector, wherein light captured by one storage unit of a pixel has a $$\frac{360}{m}$$

degree phase shift relative to light captured by another storage unit of the same pixel.

The imaging device 270 may be specially configured to detect electromagnetic radiation within the band that the illumination source 265 projects. The imaging device 270 may employ a narrowband band-pass filter which filters out light outside of the spectrum emitted by the illumination source 265. When this band is relatively small, the signal-to-noise ratio (SNR) is large, which allows images to be captured by the imaging device 270 rapidly. In some embodiments, the imaging device 270 is a high-frequency camera, but when high frequency is not needed, the imaging device 270 may capture images at a frequency less than the maximum frequency. The frame rate with which images are captured by the imaging device 270 is generally 60 Hz of greater, although some embodiments may capture images at a slower rate. The illumination source 265 may be configured to only emit light when the imaging device 270 is capturing images, i.e., the illumination source 265 and the imaging device 270 are synchronized, e.g., by the controller 310.

The imaging device 270 may capture images at a first frequency during normal operating conditions, but certain conditions may trigger the imaging device 270 to capture images at a higher frequency. For example, when the controller 310 cannot determine the position and orientation of the eye 230 based on the captured images from the imaging device 270, the scan may be considered a "bad scan." A "bad scan" may be triggered by the user blinking. In the case of a "bad scan," the scan may be disregarded and the imaging device 270 can be triggered to immediately capture another scan of the eye 230 until a successful scan is recorded. In this manner, the eye tracking system 260 can ensure that the tracking of the eye's position and orientation is as accurate and current as possible, without requiring unnecessary computation and power consumption.

The controller 310 determines depth information using the information captured by the detector of the imaging device 270. The controller 310 may determine at least one phase difference between the temporally distorted illumination pattern reflected from at least one surface of the eye 230 captured by the detector of the imaging device 270 and the temporally varying irradiance pattern emitted from the illumination source 265. The controller 310 determines the at least one phase difference associated with the at least one surface of the eye 230 based on the light intensities captured in the storage units of one or more pixels of the detector. In some embodiments, the controller 310 determines a phase difference based on one or more differences between the light intensities captured in the storage units of one pixel or a group of pixels. Each storage unit for each pixel stores an intensity of a reflected light signal that has a specific phase shift relative to another light signal whose intensity is captured in another storage unit for that pixel, wherein the captured light signals have the same carrier signal and are captured from the same surface of the eye 230. In one illustrative embodiment, each pixel in the detector of the imaging device 270 is associated with four storage units with 90 degree phase shift relative to one another. In this case, for one surface of the eye 230, the controller 310 determines a difference between a first light signal intensity captured in a first storage unit of a pixel and a second light signal intensity captured in a second storage unit of the pixel, wherein the first and second storage units has 90 degree phase shift relative to one another. Additionally, the controller 310 determines an additional difference between a third light signal intensity captured in a third storage unit of the pixel and a fourth light signal intensity captured in a fourth storage unit of the pixel, wherein the third and fourth storage units has 90 degree phase shift relative to one another. Then, the controller 310 determines the phase difference as an arctangent of a ratio of the difference to the additional difference. This process may be performed for multiple pixels of the detector of the imaging device 270, for the same or different surfaces of the eye 230.

The determined phase difference between the temporally distorted illumination pattern reflected from a surface of the eye 230 and the emitted temporally varying irradiance (control) pattern is proportional to a time-of-flight for the temporally varying irradiance pattern that is first emitted from the illumination source 265 then reflected from the surface of the eye 230 and finally detected by the imaging device 270. Based on the time-of-flight and a known frequency of a carrier signal of the temporally varying irradiance pattern, the controller 310 then calculates a distance from the detector of the imaging device 320 to the surface of the eye 230. Based on multiple calculated distances from the detector of the imaging device 320 to different surfaces of the eye 230, the controller 310 can determine three-dimensional coordinates of surfaces in at least a portion of the eye 230 and update a three-dimensional model of at least the portion of the eye 230. Finally, the controller 310 can estimate a position and orientation of the eye 230 and track the eye 230 based on the updated model of the eye 230.

In some embodiments, a varifocal module (not shown in FIG. 3) is coupled to the controller 310. The varifocal module can be configured to adjust resolution of images displayed on the electronic display 210 by performing foveated rendering of the displayed images, based on the determined position and orientation of the eye 230. In this case, the varifocal module is electrically coupled to the electronic display 210 and provides image signals associated with the foveated rendering to the electronic display 210. The varifocal module may provide a maximum pixel density for the electronic display 210 only in a foveal region of the user's eye-gaze, while a lower pixel resolution for the electronic display 210 can be used in other regions of the electronic display 210. In some embodiments, the varifocal module changes a focal plane at which images are presented to a user. The varifocal module can be configured to change the focal plane by adjusting a location of one or more optical elements of the optical assembly 220 and/or a location of the electronic display 210. The change of location of the one or more optical elements of the optical assembly 220 and/or the change of location of the electronic display 210 is based on the information about eye position/orientation obtained from the controller 310. Based on the information about user's eye-gaze, the controller 310 and/or the varifocal module determine where the eye 230 is accommodating. Then, based on the determined accommodation region, the varifocal module adjusts the location of the one or more optical elements of the optical assembly 220 and/or the electronic display 210 relative to each other, providing content that is presented to the user at the appropriate focal plane. Additional details regarding HMDs with varifocal capability are discussed in U.S. application Ser. No. 14/963,109, filed Dec. 8, 2015, and is herein incorporated by reference in its entirety.

The eye 230 includes a sclera 315, a cornea 320, a pupil 325, a lens 330, an iris 335, and a fovea 340. The sclera 315 is the relatively opaque (usually visibly white) outer portion of the eye 230, which is often referred to as the "white of the eye." The cornea 320 is the curved surface covering the iris and the pupil of the eye 230. The cornea 320 is essentially transparent in the visible band (~380 nm to 750 nm) of the electromagnetic spectrum, and the near-infrared region (up to approximately 1,400 nanometers). The lens 330 is a transparent structure which serves to focus light at the retina (the back of the eye 230). The iris 335 is a thin, colored, circular diaphragm concentric with the pupil 325. The iris 335 is the colored portion of the eye 230 which contracts to alter the size of the pupil 325, a circular hole through which light enters the eye 230. The fovea 340 is an indent on the retina. The fovea 340 corresponds to the area of highest visual acuity.

Due to the rotation and movement of the eye 230, the portion of the eye's surface illuminated by the illumination source 265 may be variable. In some embodiments, the illumination source 265 projects light in a spectrum where the cornea 320 is nearly transparent (e.g., the near infrared or visible spectrum). In the case in which part of the light pattern passes through the cornea 320 and illuminates the iris 335, the resultant illumination pattern on the approximately planar interface of the iris is temporally distorted (phase offsets) according to some optical power of the surface of the cornea 320. For the region within the pupil 325 of the iris 335, the intensity of the illumination pattern is significantly reduced. In some embodiments, the illumination pattern upon the pupil 325 is considered to be negligible. The controller 310 may identify a distorted circular unilluminated portion in the image captured by the imaging device 270 as the pupil 325 and determine the position and angular orientation of the eye 230 based on the position of the pupil 325.

In some embodiments, the illumination source 265 projects light in a spectrum where the cornea 320 is nearly opaque (e.g., infrared light with a wavelength greater than 1.5 µm) and the imaging device 270 (e.g., a long infrared camera) detects the resultant illumination pattern. When the cornea 320 is illuminated by the light pattern, the controller 310 may estimate the eye's angular orientation and/or translation based on the curvature of the cornea 320. Because the cornea 320 projects outward from the approximately ellipsoidal sclera 315, the controller 310 may estimate an orientation of the eye 230 by detecting the curvature of the cornea 320. The controller 310 may also estimate the eye's orientation by detecting the cornea-sclera interface, i.e., the roughly circular outline where the surface of the cornea 320 and the surface of the sclera 315 intersect. The controller 310 may also estimate the eye's orientation by detecting the vertex of the cornea 320, i.e., the part of the cornea 320 that extends furthest from the center of the eye 230. In this approach, a detector (sensor) of the imaging device 270 allows for both a temporal phase measurement to generate depth information leading to a three-dimensional reconstruction of the eye 230 and surrounding surfaces. Then, by summing total signal levels (ignoring phase), a classical two-dimensional image of the eye 230 and surrounding surfaces is garnered. This allows both three-dimensional and two-dimensional data sets to be generated simultaneously.

The eye's pupillary axis 345 and foveal axis 350 are also depicted in FIG. 3. The pupillary axis 345 and foveal axis 350 change as the eye 230 moves. In FIG. 3, the eye 230 is depicted with a horizontal pupillary axis 345. Accordingly, the foveal axis 350 in FIG. 3 may point about 6° below the horizontal plane. FIG. 3 shows an illustrative embodiment of the eye tracking system 260 where the illumination source 265 and the imaging device 270 are positioned outside a visual field of the eye 230. Different layouts for the illumination source 265 and the imaging device 270 than the one shown in FIG. 3 are also supported, e.g., a layout where the illumination source 265 and the imaging device 270 are positioned on different sides from the pupillary axis 345.

Figure 4:
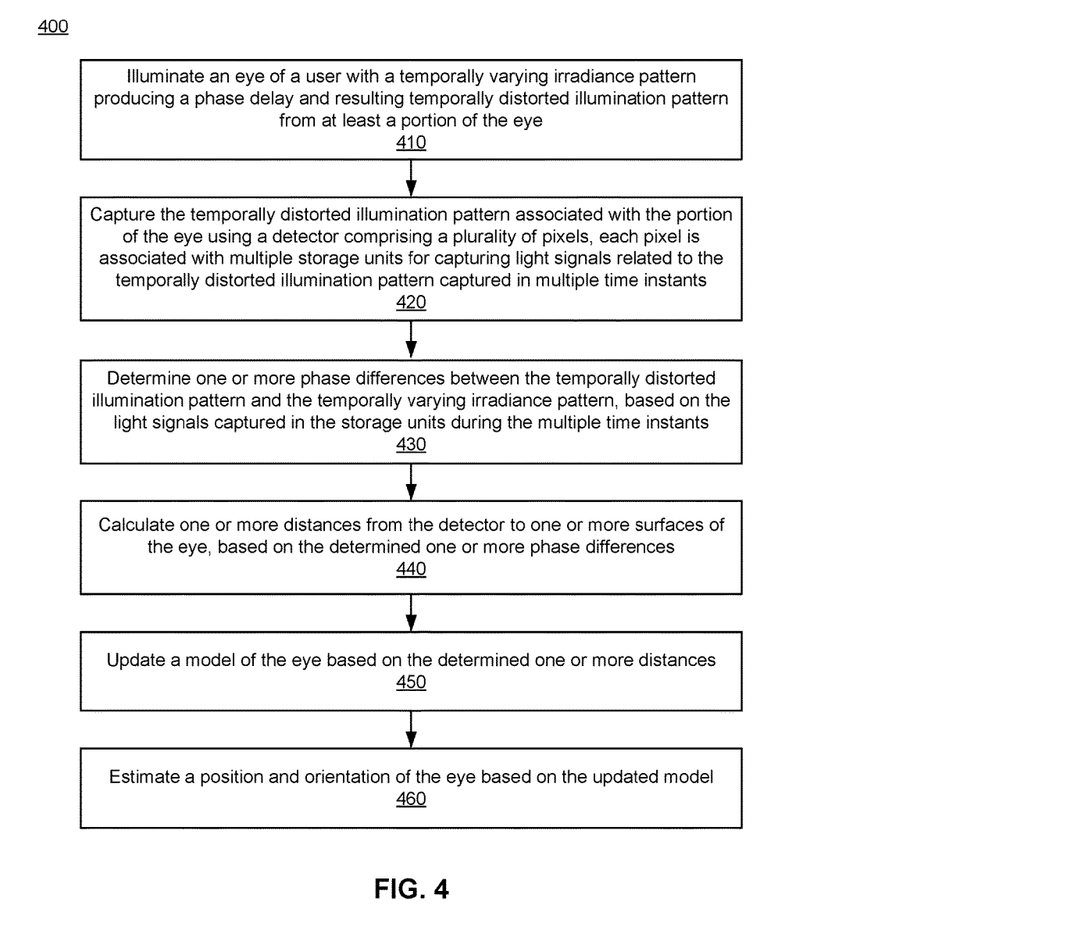
FIG. 4 is a flow chart illustrating a process of determining eye tracking information based on time-of-flight information, which may be implemented at the HMD shown in FIG. 1, in accordance with an embodiment.

FIG. 4 is a flow chart illustrating a process 400 of determining eye tracking information based on time-of-flight, which may be implemented at the HMD 100 shown in FIG. 1, in accordance with an embodiment. The process 400 of FIG. 4 may be performed by the components of a HMD (e.g., the HMD 100). Other entities may perform some or all of the steps of the process in other embodiments. Likewise, embodiments may include different and/or additional steps, or perform the steps in different orders.

The HMD illuminates 410 (via an illumination source) an eye of a user wearing the HMD with a temporally varying irradiance pattern producing a phase delay and resulting temporally distorted illumination pattern from at least a portion of the eye. In some embodiments, the temporal irradiance pattern comprises a light intensity signal based on a sine wave or a square wave. In an embodiment, the light intensity signal comprises a single frequency. In an alternate embodiment, the light intensity signal comprises multiple frequencies.

The HMD captures 420 (e.g., via a detector of an imaging device) the temporally distorted illumination pattern associated with the portion of the eye. The detector comprises a plurality of pixels, wherein each pixel is associated with multiple storage units for capturing light signals related to the temporally distorted illumination pattern captured in multiple time instants. Each storage unit for each pixel in the detector captures an intensity of a received light signal that has a specific phase shift relative to another light signal whose intensity is captured in another storage unit for that pixel, wherein the captured light signals have the same carrier signal and are captured from the same surface of the eye as mapped to each pixel element. The selection of each storage unit is controlled by a controller in sync at a sub-division with a driving phase and a frequency of the illumination source.

The HMD determines 430 (e.g., via a controller coupled to the imaging device) one or more phase differences between the temporally distorted illumination pattern and the temporally varying irradiance pattern, based on the light signals captured in the storage units during the multiple time instants. In some embodiments, the HMD determines a phase difference based on differences between the light signals captured in the storage units of one pixel or a group of pixels. In one embodiment, each pixel in the detector is associated with four storage units with 90 degree phase shift (as based upon an illumination frequency) relative to one another. In this case, for one surface of the eye, the HMD determines a difference between a first light signal intensity captured in a first storage unit of a pixel and a second light signal intensity captured in a second storage unit of the pixel, wherein the first and second storage units have a 90 degree phase shift relative to one another. Additionally, the HMD determines an additional difference between a third light signal intensity captured in a third storage unit of the pixel and a fourth light signal intensity captured in a fourth storage unit of the pixel, wherein the third and fourth storage units have a 90 degree phase shift relative to one another. The HMD determines 430 the phase difference as an arctangent of a ratio of the difference to the additional difference. A phase difference between the temporally distorted illumination pattern reflected from a surface of the eye and the emitted temporally varying irradiance pattern is proportional to a time-of-flight for the emitted temporally varying irradiance pattern to be reflected from the surface of the eye and then detected by the detector of the imaging device.

The HMD calculates 440 (e.g., via the controller) one or more distances from the detector to one or more surfaces of the eye, based on the determined one or more phase differences between the temporally distorted illumination pattern and the emitted temporally varying irradiance pattern.

The HMD updates 450 (e.g., via the controller) a model of the eye based on the determined one or more distances. In some embodiments, the HMD generates an initial model of the eye or receives the initial model of the eye from, e.g., a console coupled to the HMD. In some embodiments, the HMD determines a shape of the portion of the eye based on the temporally distorted illumination pattern captured by the imaging device in different time instants. The HMD updates 450 the model of the eye based on the determined shape of the portion of the eye. In some embodiments, the HMD determines three-dimensional coordinates of at least one of a cornea, a sclera and a pupil of the eye, based on the temporally distorted illumination pattern captured by the imaging device in the different time instants. The HMD updates 450 the model of the eye based on the determined three-dimensional coordinates.

The HMD estimates 460 (e.g., via the controller) a position and orientation of the eye based on the updated model of the eye. In some embodiments, the HMD estimates position and orientation of both eyes of the user, based on models updated for both eyes. The various applications of the HMD based on the estimated position and orientation of the user's eye include, but are not limited to, providing user interfaces (e.g., gaze-based selection), attention estimation (e.g., for user safety), gaze-contingent display modes (e.g., foveated rendering, varifocal optics, adaptive optical distortion correction, synthetic depth of field rendering), metric scaling for depth and parallax correction (e.g., IPD and eye-box adjustment), etc. In some embodiments, the HMD adjusts (e.g., via a varifocal module coupled to the controller) presentation of one or more images displayed at an electronic display of the HMD, based on the estimated position and orientation of the eye. In an embodiment, the HMD performs (e.g., via the varifocal module) foveated rendering of the displayed images, based on the estimated orientation of the eye. Alternatively or additionally, the varifocal module can use information about the position and orientation of the user's eye obtained from the controller to adjust where objects are displayed to mitigate vergence-accommodation conflict.

System Environment

Figure 5:
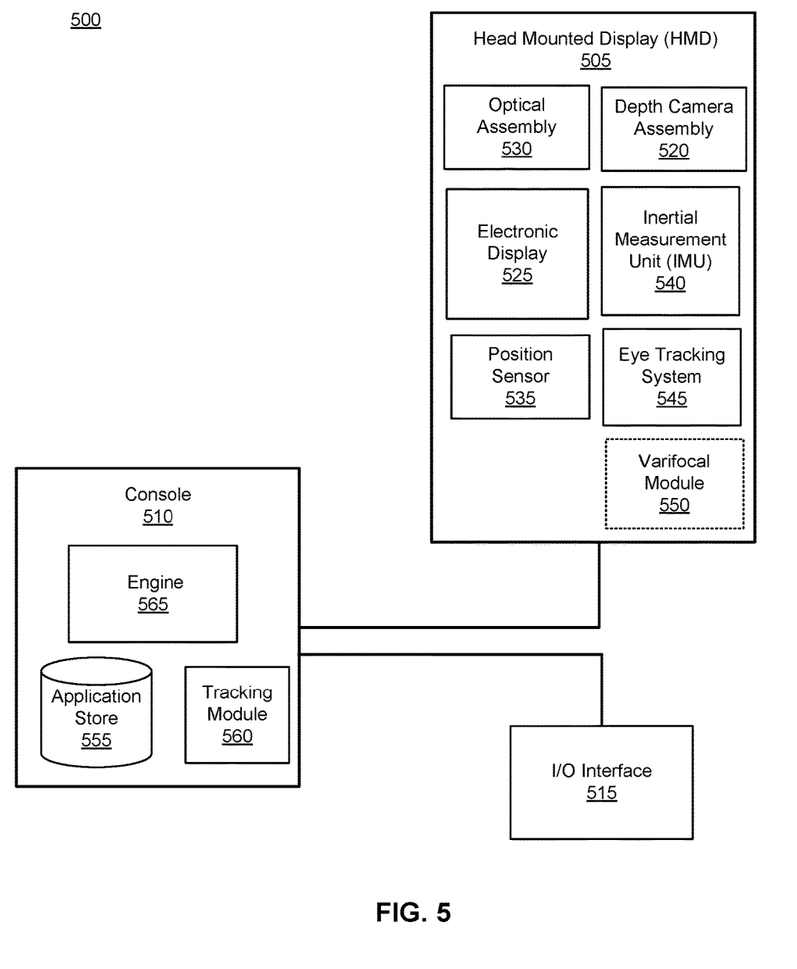
FIG. 5 is a block diagram of a system environment that includes the HMD shown in FIG. 1 with integrated eye tracking, in accordance with an embodiment.

FIG. 5 is a block diagram of one embodiment of a HMD system 500 in which a console 510 operates. The HMD system 500 may operate in a VR system environment, an AR system environment, a MR system environment, or some combination thereof. The HMD system 500 shown by FIG. 5 comprises a HMD 505 and an input/output (I/O) interface 515 that is coupled to the console 510. While FIG. 5 shows an example HMD system 500 including one HMD 505 and on I/O interface 515, in other embodiments any number of these components may be included in the HMD system 500. For example, there may be multiple HMDs 505 each having an associated I/O interface 515, with each HMD 505 and I/O interface 515 communicating with the console 510. In alternative configurations, different and/or additional components may be included in the HMD system 500. Additionally, functionality described in conjunction with one or more of the components shown in FIG. 5 may be distributed among the components in a different manner than described in conjunction with FIG. 5 in some embodiments. For example, some or all of the functionality of the console 510 is provided by the HMD 505.

The HMD 505 is a head-mounted display that presents content to a user comprising virtual and/or augmented views of a physical, real-world environment with computer-generated elements (e.g., two-dimensional or three-dimensional images, two-dimensional or three-dimensional video, sound, etc.). In some embodiments, the presented content includes audio that is presented via an external device (e.g., speakers and/or headphones) that receives audio information from the HMD 505, the console 510, or both, and presents audio data based on the audio information. The HMD 505 may comprise one or more rigid bodies, which may be rigidly or non-rigidly coupled together. A rigid coupling between rigid bodies causes the coupled rigid bodies to act as a single rigid entity. In contrast, a non-rigid coupling between rigid bodies allows the rigid bodies to move relative to each other. An embodiment of the HMD 505 is the HMD 100 described above in conjunction with FIG. 1.

The HMD 505 includes a DCA 520, an electronic display 525, an optical assembly 530, one or more position sensors 535, an IMU 540, an eye tracking system 545, and an optional varifocal module 550. Some embodiments of the HMD 505 have different components than those described in conjunction with FIG. 5. Additionally, the functionality provided by various components described in conjunction with FIG. 5 may be differently distributed among the components of the HMD 505 in other embodiments.

The DCA 520 captures data describing depth information of an area surrounding the HMD 505. The data describing depth information may be associated with one or a combination of the following techniques used to determine depth information: structured light, time-of-flight, or some combination thereof. The DCA 520 can compute the depth information using the data, or the DCA 520 can send this information to another device such as the console 510 that can determine the depth information using data from the DCA 520.

The DCA 520 includes an illumination source, an imaging device, and a controller. The illumination source emits light onto an area surrounding the HMD. In some embodiments, the illumination source includes a plurality of emitters on a single substrate. The imaging device captures ambient light and light from one or more emitters of the plurality of emitters of the plurality of emitters that is reflected from objects in the area. The controller coordinates how the illumination source emits light and how the imaging device captures light. In some embodiments, the controller may also determine depth information associated with the local area using the captured images.

In some embodiments, the illumination source of the DCA 520 includes a plurality of emitters that each emits light having certain characteristics (e.g., wavelength, polarization, coherence, temporal behavior, etc.). The characteristics may be the same or different between emitters, and the emitters can be operated simultaneously or individually. In one embodiment, the plurality of emitters could be, e.g., laser diodes (e.g., edge emitters), inorganic or organic light emitting diodes (LEDs), a vertical-cavity surface-emitting laser (VCSEL), or some other source. In some embodiments, a single emitter or a plurality of emitters in the illumination source can emit light having a structured light pattern.

The electronic display 525 displays two-dimensional or three-dimensional images to the user in accordance with data received from the console 510. In various embodiments, the electronic display 525 comprises a single electronic display or multiple electronic displays (e.g., a display for each eye of a user). Examples of the electronic display 525 include: a liquid crystal display (LCD), an organic light emitting diode (OLED) display, an inorganic light emitting diode (ILED) display, an active-matrix organic light-emitting diode (AMOLED) display, a transparent organic light emitting diode (TOLED) display, some other display, or some combination thereof.

The optical assembly 530 magnifies image light received from the electronic display 525, corrects optical errors associated with the image light, and presents the corrected image light to a user of the HMD 505. The optical assembly 530 includes a plurality of optical elements. Example optical elements included in the optical assembly 530 include: an aperture, a Fresnel lens, a convex lens, a concave lens, a filter, a reflecting surface, or any other suitable optical element that affects image light. Moreover, the optical assembly 530 may include combinations of different optical elements. In some embodiments, one or more of the optical elements in the optical assembly 530 may have one or more coatings, such as partially reflective or anti-reflective coatings.

Magnification and focusing of the image light by the optical assembly 530 allows the electronic display 525 to be physically smaller, weigh less and consume less power than larger displays. Additionally, magnification may increase the field of view of the content presented by the electronic display 525. For example, the field of view of the displayed content is such that the displayed content is presented using almost all (e.g., approximately 110 degrees diagonal), and in some cases all, of the user's field of view. Additionally, in some embodiments, the amount of magnification may be adjusted by adding or removing optical elements.

In some embodiments, the optical assembly 530 may be designed to correct one or more types of optical error. Examples of optical error include barrel or pincushion distortions, longitudinal chromatic aberrations, or transverse chromatic aberrations. Other types of optical errors may further include spherical aberrations, chromatic aberrations or errors due to the lens field curvature, astigmatisms, or any other type of optical error. In some embodiments, content provided to the electronic display 525 for display is pre-distorted, and the optical assembly 530 corrects the distortion when it receives image light from the electronic display 525 generated based on the content.

The IMU 540 is an electronic device that generates data indicating a position of the HMD 505 based on measurement signals received from one or more of the position sensors 535 and from depth information received from the DCA 520. A position sensor 535 generates one or more measurement signals in response to motion of the HMD 505. Examples of position sensors 535 include: one or more accelerometers, one or more gyroscopes, one or more magnetometers, another suitable type of sensor that detects motion, a type of sensor used for error correction of the IMU 540, or some combination thereof. The position sensors 535 may be located external to the IMU 540, internal to the IMU 540, or some combination thereof.

Based on the one or more measurement signals from one or more position sensors 535, the IMU 540 generates data indicating an estimated current position of the HMD 505 relative to an initial position of the HMD 505. For example, the position sensors 535 include multiple accelerometers to measure translational motion (forward/back, up/down, left/right) and multiple gyroscopes to measure rotational motion (e.g., pitch, yaw, roll). In some embodiments, the IMU 540 rapidly samples the measurement signals and calculates the estimated current position of the HMD 505 from the sampled data. For example, the IMU 540 integrates the measurement signals received from the accelerometers over time to estimate a velocity vector and integrates the velocity vector over time to determine an estimated current position of a reference point on the HMD 505. Alternatively, the IMU 540 provides the sampled measurement signals to the console 510, which interprets the data to reduce error. The reference point is a point that may be used to describe the position of the HMD 505. The reference point may generally be defined as a point in space or a position related to the HMD's 505 orientation and position.

The IMU 540 receives one or more parameters from the console 510. The one or more parameters are used to maintain tracking of the HMD 505. Based on a received parameter, the IMU 540 may adjust one or more IMU parameters (e.g., sample rate). In some embodiments, certain parameters cause the IMU 540 to update an initial position of the reference point so it corresponds to a next position of the reference point. Updating the initial position of the reference point as the next calibrated position of the reference point helps reduce accumulated error associated with the current position estimated the IMU 540. The accumulated error, also referred to as drift error, causes the estimated position of the reference point to "drift" away from the actual position of the reference point over time. In some embodiments of the HMD 505, the IMU 540 may be a dedicated hardware component. In other embodiments, the IMU 540 may be a software component implemented in one or more processors.

The eye tracking system 545 determines eye tracking information associated with an eye of a user wearing the HMD 505. The eye tracking information determined by the eye tracking system 545 may comprise information about a position and orientation of the user's eye, i.e., information about an angle of an eye-gaze. The eye tracking system 545 comprising an illumination source and an imaging device is an embodiment of the eye-tracking system 240 described above in conjunction with FIGS. 2-4. The illumination source of the eye tracking system 545 is configured to illuminate the user's eye with a temporal irradiance light pattern. The imaging device of the eye tracking system 545 is configured to capture light reflected from at least one surface of the user's eye. The eye tracking system 545 determines the eye tracking information and tracks position/orientation of the user's eye using time-of-flight information associated with the reflected light.

In some embodiments, the varifocal module 550 is integrated into the HMD 505. The varifocal module 550 may be coupled to the eye tracking system 545 to obtain eye tracking information determined by the eye tracking system 545. The varifocal module 550 may be configured to adjust focus of one or more images displayed on the electronic display 525, based on the determined eye tracking information obtained from the eye tracking system 545. In this way, the varifocal module 550 can mitigate vergence-accommodation conflict in relation to image light. The varifocal module 550 can be interfaced (e.g., either mechanically or electrically) with the electronic display 525 and/or at least one optical element of the optical assembly 530. Then, the varifocal module 550 may be configured to adjust focus of the one or more images displayed on the electronic display 525 by adjusting position of the electronic display 525 and/or position of the at least one optical element of the optical assembly 530, based on the determined eye tracking information obtained from the eye tracking system 545. By adjusting the position, the varifocal module 550 varies focus of image light output from the electronic display 525 towards the user's eye. The varifocal module 550 may be also configured to adjust resolution of the images displayed on the electronic display 525 by performing foveated rendering of the displayed images, based at least in part on the determined eye tracking information obtained from the eye tracking system 545. In this case, the varifocal module 550 provides appropriate image signals to the electronic display 525. The varifocal module 550 provides image signals with a maximum pixel density for the electronic display 525 only in a foveal region of the user's eye-gaze, while providing image signals with lower pixel densities in other regions of the electronic display 525. The various additional applications of the varifocal module 550 based on the eye tracking information include, but are not limited to, providing user interfaces (e.g., gaze-based selection), attention estimation (e.g., for user safety), different gaze-contingent display modes (e.g., adaptive optical distortion correction, synthetic depth of field rendering), metric scaling for depth and parallax correction (e.g., IPD and eye-box adjustment), etc.

The I/O interface 515 is a device that allows a user to send action requests and receive responses from the console 510. An action request is a request to perform a particular action. For example, an action request may be an instruction to start or end capture of image or video data or an instruction to perform a particular action within an application. The I/O interface 515 may include one or more input devices. Example input devices include: a keyboard, a mouse, a game controller, or any other suitable device for receiving action requests and communicating the action requests to the console 510. An action request received by the I/O interface 515 is communicated to the console 510, which performs an action corresponding to the action request. In some embodiments, the I/O interface 515 includes an IMU 540 that captures calibration data indicating an estimated position of the I/O interface 515 relative to an initial position of the I/O interface 515. In some embodiments, the I/O interface 515 may provide haptic feedback to the user in accordance with instructions received from the console 510. For example, haptic feedback is provided when an action request is received, or the console 510 communicates instructions to the I/O interface 515 causing the I/O interface 515 to generate haptic feedback when the console 510 performs an action.

The console 510 provides content to the HMD 505 for processing in accordance with information received from one or more of: the DCA 520, the HMD 505, and the I/O interface 515. In the example shown in FIG. 5, the console 510 includes an application store 555, a tracking module 560, and an engine 565. Some embodiments of the console 510 have different modules or components than those described in conjunction with FIG. 5. Similarly, the functions further described below may be distributed among components of the console 510 in a different manner than described in conjunction with FIG. 5.

The application store 555 stores one or more applications for execution by the console 510. An application is a group of instructions, that when executed by a processor, generates content for presentation to the user. Content generated by an application may be in response to inputs received from the user via movement of the HMD 505 or the I/O interface 515. Examples of applications include: gaming applications, conferencing applications, video playback applications, or other suitable applications.

The tracking module 560 calibrates the HMD system 500 using one or more calibration parameters and may adjust one or more calibration parameters to reduce error in determination of the position of the HMD 505 or of the I/O interface 515. For example, the tracking module 560 communicates a calibration parameter to the DCA 520 to adjust the focus of the DCA 520 to more accurately determine positions of structured light elements captured by the DCA 520. Calibration performed by the tracking module 560 also accounts for information received from the IMU 540 in the HMD 505 and/or an IMU 540 included in the I/O interface 515. Additionally, if tracking of the HMD 505 is lost (e.g., the DCA 520 loses line of sight of at least a threshold number of structured light elements), the tracking module 560 may re-calibrate some or all of the HMD system 500.

The tracking module 560 tracks movements of the HMD 505 or of the I/O interface 515 using information from the DCA 520, the one or more position sensors 535, the IMU 540 or some combination thereof. For example, the tracking module 560 determines a position of a reference point of the HMD 505 in a mapping of a local area based on information from the HMD 505. The tracking module 560 may also determine positions of the reference point of the HMD 505 or a reference point of the I/O interface 515 using data indicating a position of the HMD 505 from the IMU 540 or using data indicating a position of the I/O interface 515 from an IMU 540 included in the I/O interface 515, respectively. Additionally, in some embodiments, the tracking module 560 may use portions of data indicating a position or the HMD 505 from the IMU 540 as well as representations of the local area from the DCA 520 to predict a future location of the HMD 505. The tracking module 560 provides the estimated or predicted future position of the HMD 505 or the I/O interface 515 to the engine 565.

The engine 565 generates a three-dimensional mapping of the area surrounding the HMD 505 (i.e., the "local area") based on information received from the HMD 505. In some embodiments, the engine 565 determines depth information for the three-dimensional mapping of the local area based on information received from the DCA 520 that is relevant for techniques used in computing depth. The engine 565 may calculate depth information using one or more techniques in computing depth (e.g., structured light, time-of-flight, or some combination thereof). In various embodiments, the engine 565 uses different types of information determined by the DCA 520 or a combination of types of information determined by the DCA 520.

The engine 565 also executes applications within the system environment 500 and receives position information, acceleration information, velocity information, predicted future positions, or some combination thereof, of the HMD 505 from the tracking module 560. Based on the received information, the engine 565 determines content to provide to the HMD 505 for presentation to the user. For example, if the received information indicates that the user has looked to the left, the engine 565 generates content for the HMD 505 that mirrors the user's movement in a virtual environment or in an environment augmenting the local area with additional content. Additionally, the engine 565 performs an action within an application executing on the console 510 in response to an action request received from the I/O interface 515 and provides feedback to the user that the action was performed. The provided feedback may be visual or audible feedback via the HMD 505 or haptic feedback via the I/O interface 515.

The engine 565 can be configured to utilize, in association with the console 510 and the HMD 505, the eye tracking information obtained from the eye tracking system 545 for a variety of display and interaction applications. The various applications include, but are not limited to, providing user interfaces (e.g., gaze-based selection), attention estimation (e.g., for user safety), gaze-contingent display modes (e.g., foveated rendering, varifocal optics, adaptive optical distortion correction, synthetic depth of field rendering), metric scaling for depth and parallax correction (e.g., IPD and eye-box adjustment), etc. In some embodiments, based on information about position and orientation of the user's eye received from the eye tracking system 545, the engine 565 determines resolution of the content provided to the HMD 505 for presentation to the user on the electronic display 525. The engine 565 provides the content to the HMD 505 having a maximum pixel density (maximum resolution) on the electronic display 525 in a foveal region of the user's gaze, whereas the engine 565 provides a lower pixel resolution in other regions of the electronic display 525, thus achieving less power consumption at the HMD 505 and saving computing cycles of the console 510 without compromising a visual experience of the user. In some embodiments, the engine 565 can be configured to optimize the performance of viewing optics of the HMD 505 (e.g., components of the optical assembly 530), based on the eye tracking information obtained from the eye tracking system 545. In one embodiment, the engine 565 can adjust optical distortion correction parameters of the viewing optics, e.g., to prevent vergence-accommodation conflict. In an alternate embodiment, the engine 565 can adjust focus of images displayed on the electronic display 525, e.g., to prevent vergence-accommodation conflict.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A head-mounted display (HMD) comprising:
   an electronic display configured to display content to a user wearing the HMD;
   an optical assembly configured to direct light from the electronic display to an exit pupil of an eye of the user;
   an illumination source configured to illuminate the eye with a temporally varying irradiance pattern producing a temporally distorted illumination pattern on at least a portion of the eye;
   an imaging device configured to capture the temporally distorted illumination pattern that is associated with the portion of the eye, the imaging device including a detector comprising a plurality of pixels, each pixel is associated with multiple storage units for capturing light signals related to the temporally distorted illumination pattern captured in multiple time instants; and
   a controller coupled to the imaging device, the controller configured to:
      determine one or more phase differences between the temporally distorted illumination pattern and the temporally varying irradiance pattern, based on the light signals captured in the storage units associated with one or more pixels of the detector,
      calculate one or more distances from the detector to one or more surfaces of the eye, based on the determined one or more phase differences,
      update a model of the eye based on the determined one or more distances, and
      estimate a position and orientation of the eye based on the updated model.

2. The HMD of claim 1, wherein the temporally varying irradiance pattern comprises a light intensity signal selected from a group consisting of: a sine wave, and a square wave.

3. The HMD of claim 2, wherein the light intensity signal comprises a single frequency or a single repeating time-basis.

4. The HMD of claim 1, wherein the controller is further configured to:
   determine a difference between intensities of light captured in a pair of the storage units for each pixel of a group of the pixels in the detector;
   determine an additional difference between intensities of light captured in another pair of the storage units for that pixel; and
   determine the phase difference based on a ratio of the difference to the additional difference.

5. The HMD of claim 4, wherein the controller is further configured to:
determine the phase difference as an arctangent of the difference to the additional difference.

6. The HMD of claim 1, wherein the controller is further configured to:
determine a shape of the portion of the eye based on the temporally distorted illumination pattern captured by the imaging device during the multiple time instants; and
update the model of the eye based on the determined shape of the portion of the eye.

7. The HMD of claim 1, wherein the controller is further configured to:
determine three-dimensional coordinates of at least one of a cornea, a sclera and a pupil of the eye, based on the temporally distorted illumination pattern captured by the imaging device during the multiple time instants; and
update the model of the eye based on the determined three-dimensional coordinates.

8. The HMD of claim 1, wherein the controller is further configured to:
estimate a direction of a pupillary axis of the eye based on the updated model of the eye; and
estimate a direction of a foveal axis of the eye based on the estimated direction of the pupillary axis and based on an offset between the pupillary axis and the foveal axis.

9. The HMD of claim 1, further comprising:
a varifocal module configured to adjust presentation of one or more images displayed on the electronic display, based on the estimated position and orientation of the eye.

10. The HMD of claim 1, wherein:
the illumination source comprises an infrared (IR) source that emits light in the IR; and
the imaging device comprises a camera configured to capture images in the IR.

11. The HMD of claim 1, wherein the illumination source and the imaging device are positioned outside of a primary optical path of the electronic display, and the illumination source and the imaging device use one or more non-primary optical paths to an eye-box of the user's eye.

12. The HMD of claim 11, wherein the one or more non-primary optical paths encompass at least part of the primary optical path of the electronic display.

13. The HMD of claim 1, wherein the illumination source and the imaging device are positioned between the optical assembly and a pupil of the eye.

14. The HMD of claim 1, wherein the illumination source and the imaging device are integrated within the optical assembly.

15. A method comprising:
illuminating an eye of a user with a temporally varying irradiance pattern producing a temporally distorted illumination pattern on at least a portion of the eye;
capturing the temporally distorted illumination pattern associated with the portion of the eye using a detector comprising a plurality of pixels, each pixel is associated with multiple storage units for capturing light signals related to the temporally distorted illumination pattern captured in multiple time instants;
determining one or more phase differences between the temporally distorted illumination pattern and the temporally varying irradiance pattern, based on the light signals captured in the storage units associated with one or more pixels of the detector;
calculating one or more distances from the detector to one or more surfaces of the eye, based on the determined one or more phase differences;
updating a model of the eye based on the determined one or more distances; and
estimating a position and orientation of the eye based on the updated model.

16. The method of claim 15, wherein the temporally varying irradiance pattern comprises a light intensity signal selected from a group consisting of: a sine wave, and a square wave.

17. The method of claim 15, further comprising:
determining a difference between intensities of light captured in a pair of the storage units for each pixel of a group of the pixels in the detector;
determining an additional difference between intensities of light captured in another pair of the storage units for that pixel; and
determining the phase difference based on a ratio of the difference to the additional difference.

18. The method of claim 15, further comprising:
determining a shape of the portion of the eye based on the temporally distorted illumination pattern captured by the detector during the multiple time instants; and
updating the model of the eye based on the determined shape of the portion of the eye.

19. The method of claim 15, further comprising:
determining three-dimensional coordinates of at least one of a cornea, a sclera and a pupil of the eye, based on the distorted illumination pattern captured by the detector during the multiple time instants; and
updating the model of the eye based on the determined three-dimensional coordinates.

20. The method of claim 15, further comprising:
estimating a direction of a pupillary axis of the eye based on the updated model of the eye; and
estimating a direction of a foveal axis of the eye based on the estimated direction of the pupillary axis and based on an offset between the pupillary axis and the foveal axis.

* * * * *